(12) United States Patent
Kidooka et al.

(10) Patent No.: US 6,354,519 B1
(45) Date of Patent: Mar. 12, 2002

(54) SPRAY DEVICE FOR AN ENDOSCOPE

(75) Inventors: Satoshi Kidooka, Tokyo; Teruo Ouchi, Saitama, both of (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/703,898

(22) Filed: Nov. 2, 2000

(30) Foreign Application Priority Data

Nov. 16, 1999 (JP) ............................................ 11-324934

(51) Int. Cl.⁷ .............................. B05B 1/34; B05B 1/14; F23D 14/68
(52) U.S. Cl. ........................ 239/491; 239/463; 239/590
(58) Field of Search ................................. 239/491, 492, 239/493, 499, 463, 468, 475, 590, 469

(56) References Cited

U.S. PATENT DOCUMENTS

| | | | | |
|---|---|---|---|---|
| 3,844,484 A | * | 10/1974 | Masai | 239/404 |
| 5,067,655 A | * | 11/1991 | Farago et al. | 239/463 |
| 5,433,383 A | * | 7/1995 | Sundholm | 239/550 |
| 5,655,608 A | * | 8/1997 | Sundholm | 169/62 |
| 6,024,301 A | * | 2/2000 | Hurley et al. | 239/463 |

FOREIGN PATENT DOCUMENTS

| | | |
|---|---|---|
| JP | 7-51066 | 11/1995 |
| JP | 8-215320 | 8/1996 |

* cited by examiner

*Primary Examiner*—David A. Scherbel
*Assistant Examiner*—Davis Hwu
(74) *Attorney, Agent, or Firm*—Greenblum & Bernstein, P.L.C

(57) ABSTRACT

A spray device used for an endoscope, the spray device having a liquid transfer tube and a spray nozzle connected to a distal end of the liquid transfer tube, includes at least one spiral guide channel; a liquid whirling chamber positioned in front of at least one spiral guide channel to be connected to an outlet thereof; and an orifice formed at a center of a front inner surface of the liquid whirling chamber. The front inner surface includes a concave surface, and the concave surface is formed so that the orientation of a tangential plane at a point on the front inner surface becomes closer to the orientation of a plane normal to the axis of the spray nozzle as the point on the front inner surface approaches the axis of the spray nozzle.

10 Claims, 6 Drawing Sheets

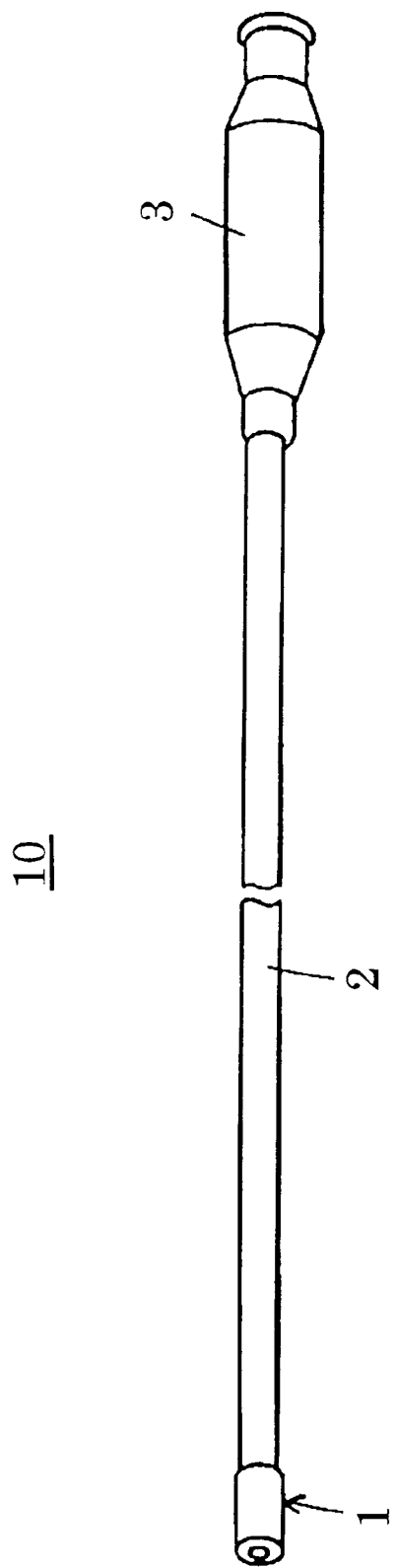

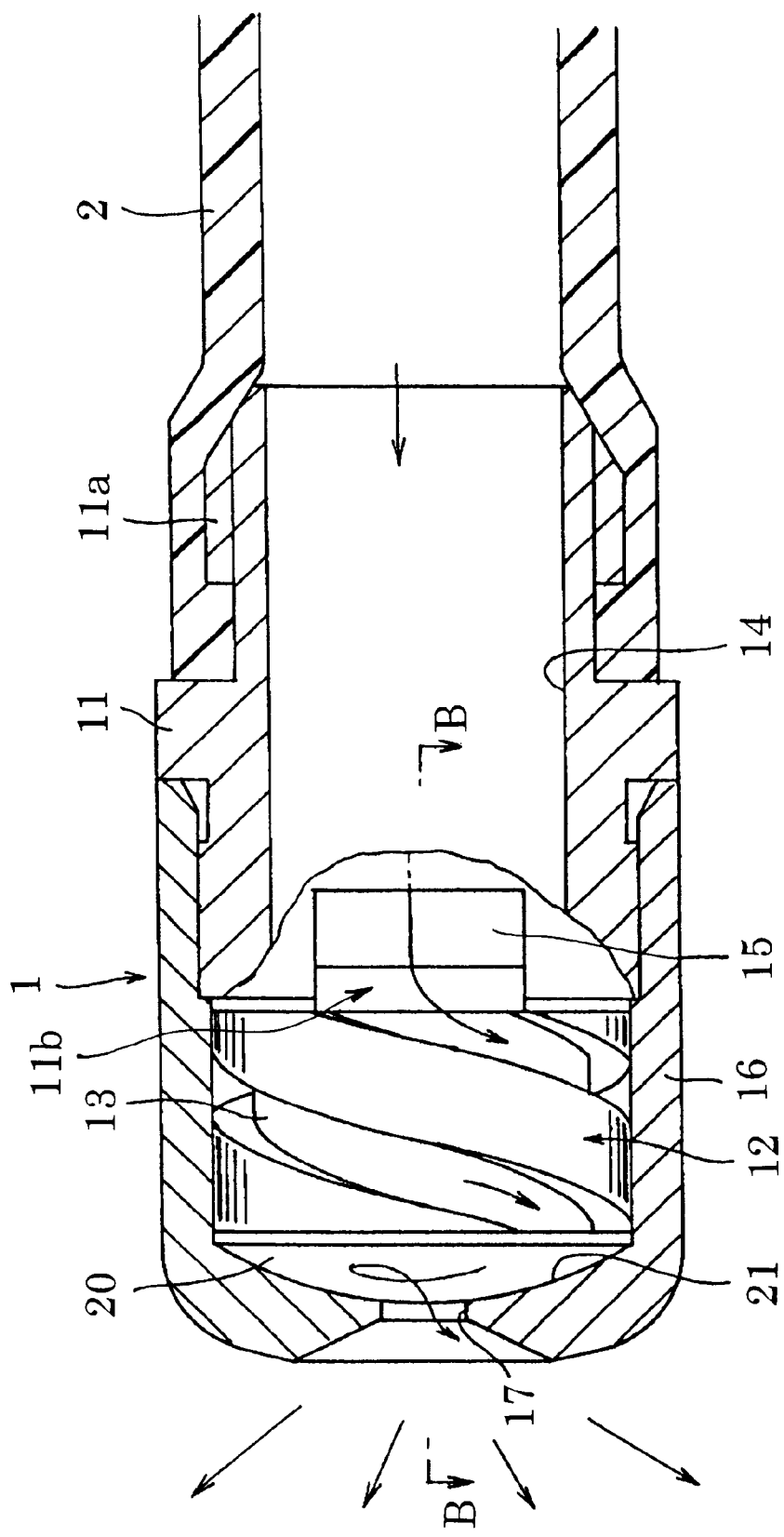

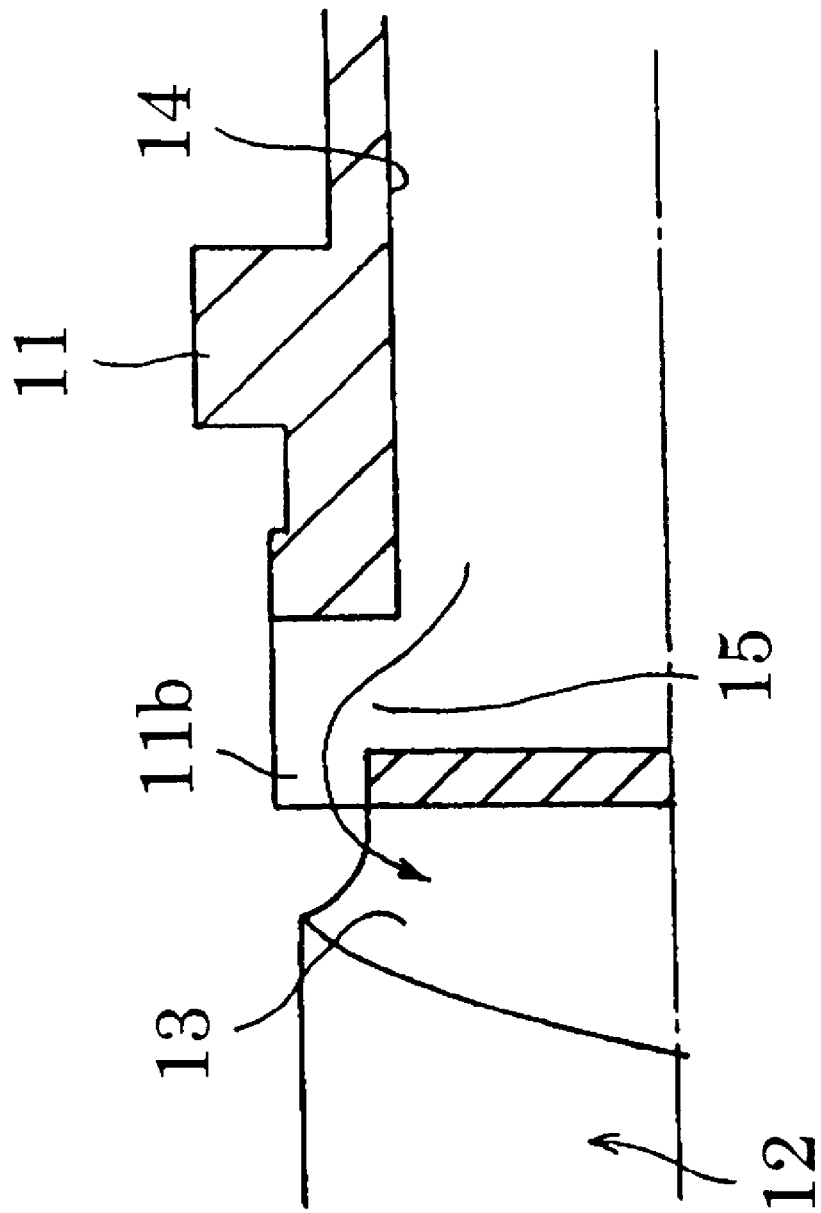

SPRAY DEVICE FOR AN ENDOSCOPE

BACKGROUND OF THE INVENTION

1. Field of the Invention

The present invention relates to a spray device for an endoscope which is inserted into a treatment tool insertion channel of the endoscope to spray a liquid in a body cavity and the like.

2. Description of the Related Art

FIG. 1 shows the distal end of a conventional spray device. The spray device can be inserted into and pulled out of a treatment tool insertion channel of an endoscope (not shown). The conventional spray device is provided with a flexible liquid transfer tube 91 which is made of an elastic material, and a spray nozzle 99 which is connected to the distal end of the liquid transfer tube 91. The spray nozzle 99 is provided, in front of the opening of the distal end of the liquid transfer tube 91, with a spiral member 92. The spiral member 92 is provided on an outer peripheral surface thereof with a spiral groove 93. The spray nozzle 99 is further provided with an end cap 94. The end cap 94 is provided at the front end thereof with an orifice 96 and is snugly fitted onto a tubular nozzle body 98 and covers the spiral member 92 in a manner so as to close the entire peripheral opening of the spiral groove 93, so that the spiral groove 93 functions as a liquid guide channel through which liquid runs from the liquid transfer tube 91 to the orifice 96. The rear end (the right end as viewed on FIG. 1) of the end cap 94 is fixedly fitted on the front end of the tubular nozzle body 98 of the spray nozzle 99, while the distal end of the liquid transfer tube 91 (with respect to the user) is fixedly fitted on the rear end of the nozzle body 98. The spray nozzle 99 is provided, in the end cap 94 between an inner end surface 97 of the end cap 94 and a front end surface (left end surface as viewed in FIG. 1) of the spiral member 92, with a liquid whirling chamber 95. An inlet and an outlet of the spiral groove (spiral channel) 93 are provided the front end of the nozzle body 98 and the liquid whirling chamber 95, respectively. The liquid whirling chamber 95 is shaped so that the liquid which spurts from the outlet of the spiral groove 93 whirls about the axis of the spray nozzle 99 (i.e., the axis of the liquid transfer tube 91) in the liquid whirling chamber 95. The axial center of the orifice 96 is coincident with that of the liquid whirling chamber 95. The inner end surface 97 of the end cap 94, which defines the front inner surface of the liquid whirling chamber 95, is formed as a circular conical surface which tapers inwards from the front end surface of the spiral member 92 to the orifice 96 (i.e., from right to left as viewed in FIG. 1).

Due to such a structure of a conventional spray device, the liquid (e.g., a medicinal liquid or a coloring liquid) which is transmitted via the liquid transfer tube 91 from the proximal end thereof spurts from the orifice 96 as a spray, having a certain spray angle, via the spiral groove 93 and the liquid whirling chamber 95 while whirling in the liquid whirling chamber 95.

The spray distribution becomes wider as the direction of the flow of the liquid spurting from the orifice 96 is closer to a circumferential direction about the axis of the spray nozzle 99. The liquid which whirls within the liquid whirling chamber 95 runs to the orifice 96 while gradually changing the direction of the flow due to the reaction force that the liquid receives from the inner end surface 97 when the liquid whirls along the inner end surface 97. FIG. 2 shows the direction of the flow of the liquid which whirls within the liquid whirling chamber 95 along the inner end surface 97 thereof in the conventional spray device. The closer the flow is to the orifice 96, the greater the angle of the direction of the flow with respect to a circumferential direction about the axis of the spray nozzle 99 (the axis of the orifice 96) becomes, since the inner end surface 97 is formed as a circular conical surface. In the particular case shown in FIG. 2, the following condition is satisfied:

θ1<θ2<θ3<θ4.

Accordingly, with such a conventional spray device, it is difficult to spray the liquid on, for example, a target inner part of the body, with a sufficient spray distribution.

SUMMARY OF THE INVENTION

It is an object of the present invention to provide a spray device for an endoscope which can spray a liquid on, for example, a target inner part of the body, with a sufficient spray distribution.

To achieve the object mentioned above, according to the present invention, a spray device used for an endoscope is provided, the spray device having a liquid transfer tube and a spray nozzle connected to a distal end of the liquid transfer tube, the spray nozzle including at least one spiral guide channel positioned in front of the distal end of the liquid transfer tube; a liquid whirling chamber positioned in front of the at least one spiral guide channel to be connected to an outlet thereof; and an orifice formed at a center of a front inner surface of the liquid whirling chamber. The front inner surface includes a concave surface, and the front inner surface is formed so that the orientation of a tangential plane lying on a point on the front inner surface becomes closer to the orientation of a plane normal to the axis of the spray nozzle as the point on the front inner surface approaches the axis of the spray nozzle.

In an embodiment, the concave surface is formed as a spherical surface.

In another embodiment, the concave surface is formed as a series of at least two circular conical surfaces which have different diameters and different taper angles with respect to the axis of the spray nozzle.

Preferably, the spray nozzle further includes a spiral member on which at least one spiral groove is formed; and an end cap on which the orifice is formed and which is snugly fitted on the spiral member in a manner so as to close an entire peripheral opening of the at least one spiral groove to define the at least one spiral guide channel.

The liquid whirling chamber is defined between the end cap and the spiral member, wherein an inner end surface of the end cap defines the front inner surface of the liquid whirling chamber 20.

Preferably, the liquid whirling chamber is shaped so that a liquid which spurts from an outlet of the at least one spiral guide channel whirls about the axis of the spray nozzle in the liquid whirling chamber, an axial center of the orifice being coincident with that of the liquid whirling chamber.

According to another aspect of the present invention, a spray nozzle is provided, which is to be fixed to a distal end of a liquid transfer tube that is inserted into and pulled out of a treatment tool insertion channel of an endoscope, the spray nozzle including at least one spiral guide channel positioned in front of the distal end of the liquid transfer tube so that an inlet of the at least one spiral guide channel is connected to the distal end of the liquid transfer tube; a liquid whirling chamber positioned in front of the at least one spiral guide channel to be connected to an outlet thereof; and an orifice provided at a center of a front inner surface of the liquid whirling chamber. The front inner surface includes a concave surface; and the concave surface is formed so that the orientation of a tangential plane lying on a point on the front inner surface changes as the point of the tangential plane on the front inner surface approaches the axis of the spray nozzle.

In an embodiment, the front inner surface is formed as a spherical surface.

In another embodiment, the front inner surface is formed as a series of at least two circular conical surfaces which have different diameters and different taper angles with respect to the axis of the spray nozzle.

The present disclosure relates to subject matter contained in Japanese Patent Application No. 11-324934 (filed on Nov. 16, 1999) which is expressly incorporated herein by reference in its entirety.

BRIEF DESCRIPTION OF THE DRAWINGS

The invention will be discussed below in detail with reference to the drawings, in which:

FIG. 3 is a perspective external view of the first embodiment of a spray device for an endoscope according to the present invention;

FIG. 4A is an axial cross sectional view of the distal end of the first embodiment of the spray device shown in FIG. 3;

FIG. 4B is an axial cross sectional view of the spray device shown in FIG. 4A as view in the direction of arrows B—B;

DESCRIPTION OF THE PREFERRED EMBODIMENTS

Figure 1:
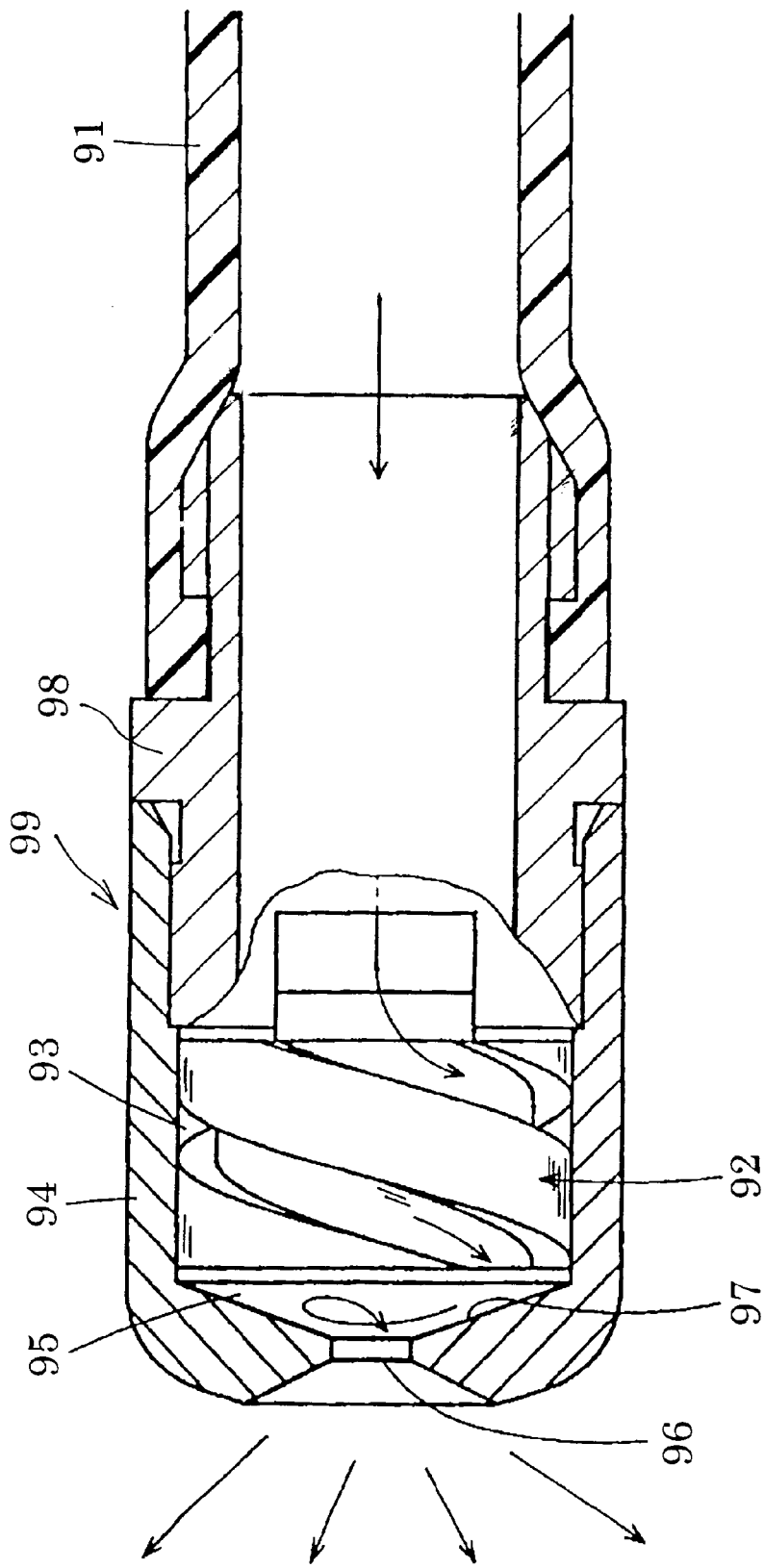
FIG. 1 is an axial cross sectional view of the distal end of a conventional spray device for an endoscope.
Figure 2:
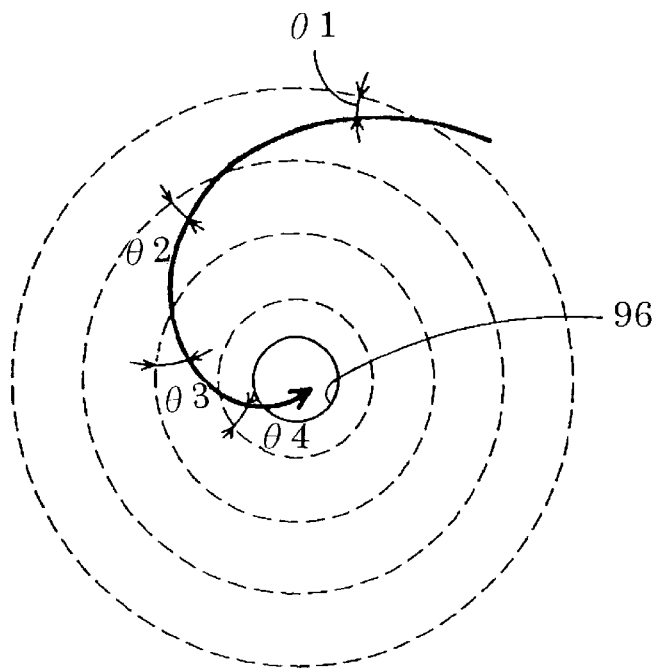
FIG. 2 is a diagram showing the direction of the flow of the liquid that whirls within the liquid whirling chamber along the front inner surface thereof in the conventional spray device shown in FIG. 1.

FIG. 3 shows the first embodiment of a spray device 10 for an endoscope according to the present invention. The first embodiment of the spray device 10 includes a spray nozzle 1, a flexible liquid transfer tube 2, and an infusion mouthpiece 3. The liquid transfer tube 2 can be inserted into and pulled out of a treatment tool insertion channel of an endoscope (not shown). The liquid transfer tube 2 is made of an elastic material such as a tetrafluorinated ethylene resin. The spray nozzle 1 is fixed to the distal end of the liquid transfer tube 2.

The infusion mouthpiece 3 is fixed to the proximal end of the liquid transfer tube 2. A syringe tube and the like can be connected to the infusion mouthpiece 3 to infuse a liquid such as a medicinal liquid or a coloring liquid into the infusion mouthpiece 3 so as to send the liquid to the spray nozzle 1 via the liquid transfer tube 2.

FIG. 4A shows the internal structure of the spray nozzle 1. The spray nozzle 1 is provided with a tubular nozzle body 11 fixed to the distal end of the liquid transfer tube 2. The nozzle body 11 is generally a cylinder-shaped and is provided, at the rear end thereof on a peripheral surface of the nozzle body 11, with a male threaded portion 11a. This male threaded portion 11a is forcibly screwed into the opening at the distal end of the liquid transfer tube 2 and is adhered thereto with an adhesive being provided between the male threaded portion 11a and a corresponding inner peripheral surface of the distal end of the liquid transfer tube 2. The spray nozzle 1 is provided immediately in front of the nozzle body 11 with a spiral member 12. The spiral member 12 is provided on an outer peripheral surface thereof with a spiral groove (spiral guide groove) 13. More than one spiral groove can be provided on the outer peripheral surface of the spiral member 12. For instance, two spiral grooves can be formed on the outer peripheral surface of the spiral member 12 in a manner similar to a double-start thread. The nozzle body 11 is provided along the axis thereof with a channel 14, so that the axis thereof coincides with the axis of the spray nozzle 1. The channel 14 is connected with the spiral groove 13 via an opening 11b and a groove 15 which are formed at the front end of the nozzle body 11 as shown FIG. 4B. The spray nozzle 1 is further provided with an end cap 16. The end cap 16 is provided at the front end thereof with an orifice 17 and is snugly fitted on substantially a front half of the nozzle body 11 in a manner so as to close the entire peripheral opening of the spiral groove 13. Due to this structure, the spiral groove 13 functions as a liquid guide channel through which liquid runs from the liquid transfer tube 2 to the orifice 17.

The spray nozzle 1 is provided, in the end cap 16 between an inner end surface 21 of the end cap 16 and a front end surface (left end surface as viewed in FIG. 4A) of the spiral member 12, with a liquid whirling chamber 20. The inlet and outlet of the spiral groove (spiral channel) 13 are connected with the front end of the nozzle body 11 and the liquid whirling chamber 20, respectively. The liquid whirling chamber 20 is shaped so that the liquid, which spurts from the outlet of the spiral groove 13, whirls about the axis of the spray nozzle 1 (i.e., the axis of the liquid transfer tube 2) in the liquid whirling chamber 20. The axial center of the orifice 17 is coincident with that of the liquid whirling chamber 20. The front end surface of the spiral member 12, which defines the rear inner surface of the liquid whirling chamber 20, is formed as a flat surface which extends orthogonal to the axis of the spray nozzle 1. On the other hand, the inner end surface 21 of the end cap 16, which defines the front inner surface of the liquid whirling chamber 20, is formed as a concave spherical surface. Therefore, the orientation of a tangential plane lying on a point on the inner end surface 21 is not constant over the entire surface thereof, but becomes increasing closer to the orientation of a normal plane of the axis of the spray nozzle 1, as the point on which the tangential plane on the inner end surface 21 lies approaches the axis of the spray nozzle. Due to such structure of the spray device 1, the liquid (e.g., a medicinal liquid or a coloring liquid) which is transmitted via the liquid transfer tube 2 from the proximal end thereof spurts from the orifice 17 as spray via the spiral groove 13 and the liquid whirling chamber 20 while whirling in the liquid whirling chamber 20.

At this time, the liquid which whirls within the liquid whirling chamber 20 runs to the orifice 17 while gradually changing the direction of the flow due to the reaction force that the liquid receives from the inner end surface 21 when the liquid whirls along the inner end surface 21.

Figure 5:
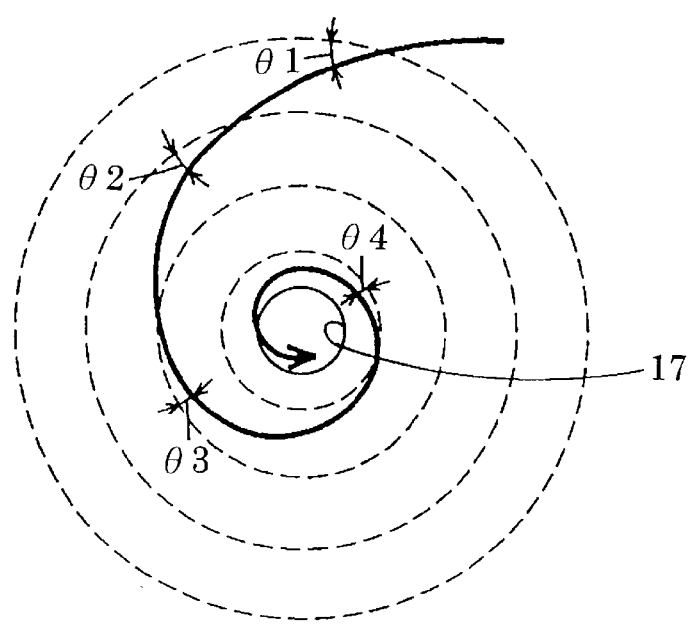
FIG. 5 is a diagram, similar to that of FIG. 2, which shows the direction of the flow of the liquid that whirls within the liquid whirling chamber along the front inner surface thereof in the first embodiment of the spray device shown in FIG. 3.

FIG. 5 shows the direction of the flow of the liquid which whirls within the liquid whirling chamber 20 along the front-end surface thereof in the spray device 1. Since the inner end surface 21 is formed as a spherical surface, the closer the flow is to the orifice 17, the closer the direction of the flow is to a circumferential direction about the axis of the spray nozzle 1 (the axis of the orifice 17). In the particular case shown in FIG. 5, the following condition is satisfied:

$\theta 1 > \theta 2 > \theta 3 > \theta 4$.

Consequently, with the present embodiment of the spray device 1, the liquid is sprayed on, for example, a target inner part of the body, with a sufficient spray distribution since the direction of the liquid spurting from the orifice 17 is nearly in line with the circumference of the orifice 17 about the axis of the spray nozzle 1.

The present invention is not limited solely to the above-illustrated embodiment. For instance, although the inner end surface 21 of the end cap 16, which defines the front inner surface of the liquid whirling chamber 20, is formed as a concave spherical surface, the inner end surface 21 does not always have to be formed as such a spherical surface. The inner end surface 21 only needs to be formed as a concave surface so that the orientation of a tangential plane lying on a point on the front inner surface (i.e., the inner end surface 21) of the liquid whirling chamber 20 gradually becomes closer to the orientation of a normal plane of the axis of the spray nozzle 1.

Figure 6:
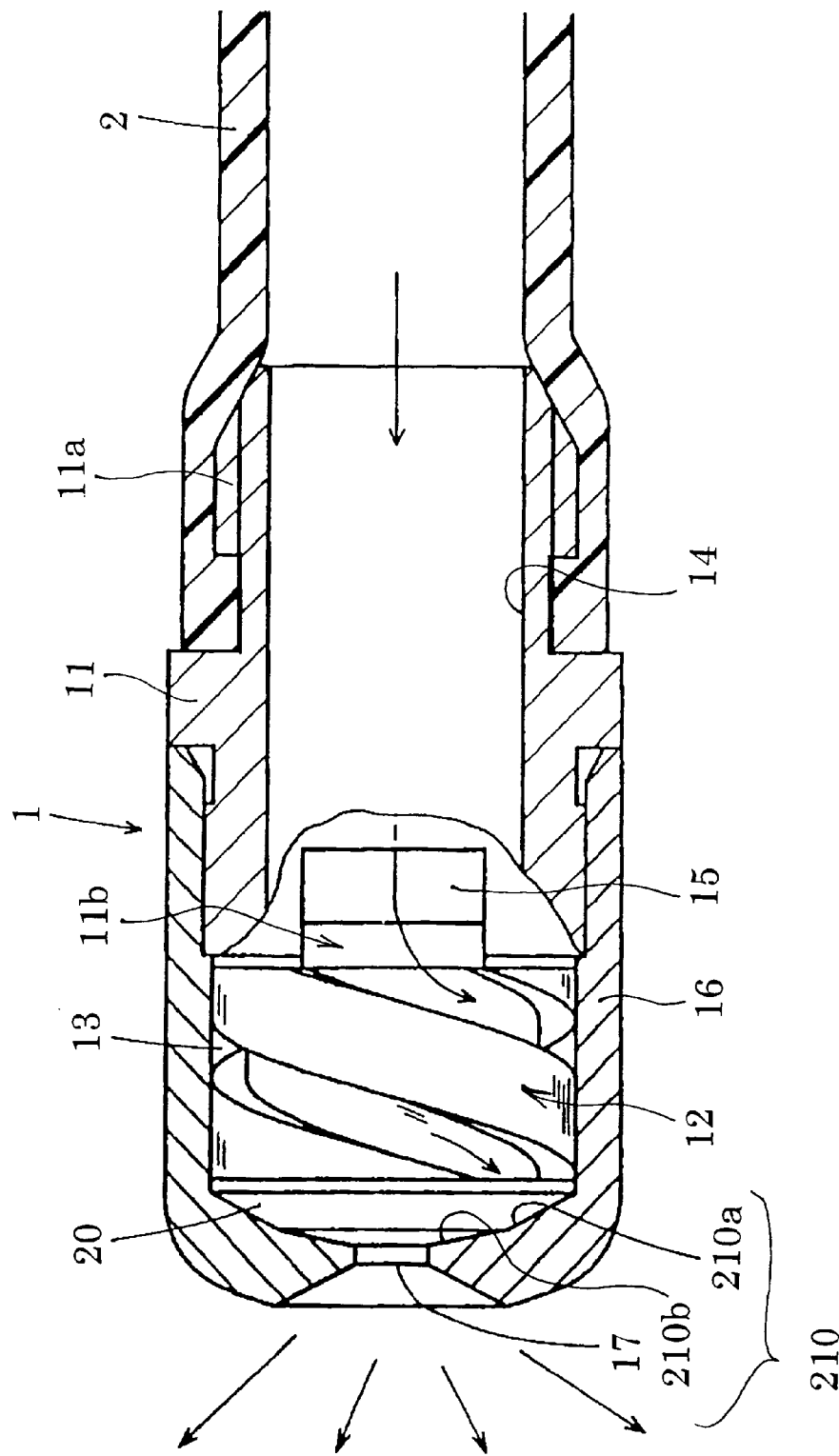
FIG. 6 is an axial cross sectional view of the distal end of the second embodiment of the spray device for an endoscope according to the present invention.

FIG. 6 shows the second embodiment of the spray device for an endoscope according to the present invention. The second embodiment of the spray device is identical to the first embodiment of the spray device except for the difference in shape of the inner end surface of the end cap 16 (i.e., the front inner surface of the liquid whirling chamber 20). In the second embodiment of the spray device 1, the inner end surface 210 of the liquid whirling chamber 20, which corresponds to the inner surface 21 of the same in the first embodiment of the spray device 1, is formed as a combination of two circular conical surfaces 210a and 210b which taper from the front end surface of the spiral member 12 to the orifice 17 (i.e., inward from right to left as viewed in FIG. 6) and have different angles with respect to the axis of the spray nozzle 1. The angle of the circular conical surface (front circular conical surface) 210b, which is positioned closer to the axis of the spray nozzle 1 than the other circular conical surface (rear circular conical surface) 210a, is closer to a right angle with respect to the axis of the spray nozzle 1 than that of the other circular conical surface 210a. As can be understood by those skilled in the art, the inner end surface of the liquid whirling chamber 20 can be formed as a combination of more than two circular conical surfaces. Moreover, the inner end surface of the liquid whirling chamber 20 can be formed as a combination of at least one circular conical surface and at least one spherical surface. Although the spiral member 12 is provided with the spiral groove 13 having a particular shape in each of the above first and second embodiments so that the liquid, which spurts from the outlet of the spiral groove 13, whirls about the axis of the spray nozzle 1 in the liquid whirling chamber 20, the shape of the spiral groove formed on the spiral member 12 is not limited solely to the particular shape shown in FIGS. 4A and 6, but can be any other shape as long as the liquid which spurts from the outlet of the spiral groove 13 whirls about the axis of the spray nozzle 1 in the liquid whirling chamber 20 properly.

As can be understood from the foregoing, according to the spray device for an endoscope to which the present invention is applied, since the front inner surface is a concave surface, and the front inner surface is formed so that the orientation of a tangential plane at a point on the front inner surface gradually becomes closer to the orientation of a plane normal to the axis of the spray nozzle as the point on the front inner surface approaches the axis of the spray nozzle, the closer the flow of the liquid which whirls within the liquid whirling chamber along the front end surface thereof is to the orifice of the spray nozzle, and the closer the direction of the flow is to a circumferential direction about the axis of the spray nozzle. Consequently, the liquid can be sprayed on, for example, a target inner part of the body, with a sufficient spray distribution which is advantageous when a liquid such as a medicinal liquid or a coloring liquid is sprayed on a target inner part of the body.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. A spray device used for an endoscope, said spray device having a liquid transfer tube and a spray nozzle connected to a distal end of said liquid transfer tube, said spray nozzle comprising:

at least one spiral guide channel positioned in front of said distal end of said liquid transfer tube;

a liquid whirling chamber positioned in front of said at least one spiral guide channel to be connected to an outlet of said at least one spiral guide channel;

an orifice provided at a center of a front inner surface of said liquid whirling chamber, said front inner surface comprising a concave spherical surface; and wherein an orientation of a plane tangential to a point on said front inner surface approaches an orientation of a plane normal to an axis of the spray nozzle as said point on said front inner surface approaches the axis of the spray nozzle.

2. The spray device according to claim 1, wherein said concave surface is formed as a series of at least two circular conical surfaces which have different diameters and different taper angles with respect to said axis of said spray nozzle.

3. The spray device according to claim 1, wherein said spray nozzle further comprises:

a spiral member on which at least one spiral groove is formed; and an end cap on which said orifice is formed and which is snugly fitted on said spiral member in a manner so as to close an entire peripheral opening of said at least one spiral groove to define said at least one spiral guide channel.

4. The spray device according to claim 3, wherein said liquid whirling chamber is defined between said end cap and said spiral member, wherein an inner end surface of said end cap defines said front inner surface of said liquid whirling chamber.

5. The spray device according to claim 3, wherein said liquid whirling chamber is shaped so that a liquid which spurts from an outlet of said at least one spiral guide channel whirls about said axis of said spray nozzle in said liquid whirling chamber, an axial center of said orifice being coincident with that of said liquid whirling chamber.

6. The spray device used for an endoscope according to claim 1, a direction of liquid ejected from said orifice being substantially aligned with a circumference of said orifice about the axis of said spray nozzle.

7. A spray nozzle which is to be fixed to a distal end of a liquid transfer tube that is inserted into and pulled out of a treatment tool insertion channel of an endoscope, said spray nozzle comprising:
- at least one spiral guide channel positioned in front of said distal end of said liquid transfer tube so that an inlet of said at least one spiral guide channel is connected to said distal end of said liquid transfer tube;
- a liquid whirling chamber positioned in front of said at least one spiral guide channel to be connected to an outlet of said at least one spiral guide channel;
- an orifice provided at a center of a front inner surface of said liquid whirling chamber, said front inner surface comprising a concave spherical surface; and
- wherein an orientation of a plane tangential to a point on said front inner surface changes as a tangent point of said plane on said front inner surface approaches an axis of said spray nozzle.

8. The spray nozzle according to claim 7, wherein said front inner surface is formed as a series of at least two circular conical surfaces which have different diameters and different taper angles with respect to said axis of said spray nozzles.

9. The spray nozzle according to claim 7, a direction of liquid ejected from said orifice being substantially aligned with a circumference of said orifice about the axis of said spray nozzle.

10. A spray device for an endoscope, said spray device having a liquid transfer tube and a spray nozzle connected to a distal end of said liquid transfer tube, said spray nozzle comprising:
- at least one spiral guide channel positioned in front of said distal end of said liquid transfer tube;
- a liquid whirling chamber positioned in front of said at least one spiral guide channel and configured to be connected to an outlet of said at least one spiral guide channel;
- an orifice provided at a center of a front inner surface of said liquid whirling chamber, said front inner surface of said liquid whirling chamber comprising an arcuate concave surface; and
- wherein an orientation of a plane tangential to a point on said arcuate concave surface approaches an orientation of a plane normal to an axis of said spray nozzle as said point on said arcuate concave surface approaches the axis of said spray nozzle.

* * * * *